US012031928B2

(12) United States Patent
Chin et al.

(10) Patent No.: US 12,031,928 B2
(45) Date of Patent: Jul. 9, 2024

(54) SCANNING MODE APPLICATION OF NEUTRON-INDUCED GAMMA ANALYSIS FOR SOIL CARBON MAPPING

(71) Applicants: AUBURN UNIVERSITY, Auburn, AL (US); THE UNITED STATES OF AMERICA, AS REPRESENTED BY THE SECRETARY OF AGRICULTURE, Washington, DC (US)

(72) Inventors: Bryan A. Chin, Auburn, AL (US); Henry Allen Torbert, III, Opelika, AL (US); Galina N. Yakubova, Auburn, AL (US); Aleksandr Kavetskiy, Auburn, AL (US); Nikolay Sargsyan, Auburn, AL (US)

(73) Assignees: AUBURN UNIVERSITY, Auburn, AL (US); THE UNITED STATES OF AMERICA, AS REPRESENTED BY THE SECRETARY OF AGRICULTURE, Washington, DC (US)

(*) Notice: Subject to any disclaimer, the term of this patent is extended or adjusted under 35 U.S.C. 154(b) by 42 days.

(21) Appl. No.: 17/841,952

(22) Filed: Jun. 16, 2022

(65) Prior Publication Data
US 2022/0326408 A1 Oct. 13, 2022

Related U.S. Application Data

(63) Continuation of application No. 16/706,013, filed on Dec. 6, 2019, now Pat. No. 11,397,277.
(Continued)

(51) Int. Cl.
*G01N 23/221* (2006.01)
*A01C 21/00* (2006.01)
(Continued)

(52) U.S. Cl.
CPC ......... *G01N 23/222* (2013.01); *A01C 21/007* (2013.01); *G01N 23/22* (2013.01);
(Continued)

(58) Field of Classification Search
CPC .... G01N 23/22; G01N 23/221; G01N 23/222; G01N 2223/074; G01N 2223/0745;
(Continued)

(56) References Cited

U.S. PATENT DOCUMENTS 3,662,179 A 5/1972 Frentrop et al.
3,833,809 A 9/1974 Beil
(Continued)

OTHER PUBLICATIONS

Yakubova, G., et al. Applying Monte-Carlo simulations to optimize an inelastic neutron scattering system for soil carbon analysis. Appl Radiat Isot. Oct. 2017;128:237-248. doi: 10.1016/j.apradiso.2017.07.003. Epub Jul. 5, 2017. PMID: 28743068.
(Continued)

*Primary Examiner* — Allen C. Ho
(74) *Attorney, Agent, or Firm* — Barnes & Thornburg LLP

(57) ABSTRACT

A system for analyzing soil content of a field includes a data acquisition unit configured to detect gamma spectra of each of a plurality of soil samples, wherein a surface area of the field is divided into a plurality of portions and the plurality of soil samples comprises at least one soil sample from each of the plurality of portions, a navigation unit configured to detect geographic coordinates of each of the plurality of soil samples, a data analysis unit configured to associate the detected gamma spectra of each of the plurality of soil samples with the geographic coordinates of the soil sample and determine a weight percent of at least one element within each of the soil samples based on the detected gamma spectra, and an element content map unit configured to
(Continued)

generate a map indicating concentration of the at least one element within the soil of the field.

19 Claims, 11 Drawing Sheets

Related U.S. Application Data

(60) Provisional application No. 62/776,822, filed on Dec. 7, 2018.

(51) Int. Cl.
| | | |
|---|---|---|
| *G01N 23/22* | (2018.01) | |
| *G01N 23/222* | (2006.01) | |
| *G01N 23/223* | (2006.01) | |
| *G01V 5/02* | (2006.01) | |
| *G01V 5/22* | (2024.01) | |

(52) U.S. Cl.
CPC ......... *G01N 23/221* (2013.01); *G01N 23/223* (2013.01); *G01V 5/22* (2024.01); *G01V 5/232* (2024.01); *G01V 5/234* (2024.01); *G01N 2223/0745* (2013.01)

(58) Field of Classification Search
CPC .. G01V 5/0016; G01V 5/0025; G01V 5/0033; G01V 5/0066; G01V 5/0069
USPC .................................................. 376/159–166
See application file for complete search history.

(56) References Cited

U.S. PATENT DOCUMENTS

| | | | | |
|---|---|---|---|---|
| 3,925,659 A | * | 12/1975 | Paap | G01V 5/102 |
| | | | | 376/163 |
| 3,930,153 A | * | 12/1975 | Scott | G01V 5/102 |
| | | | | 376/160 |
| 3,930,154 A | * | 12/1975 | Scott | G01V 5/102 |
| | | | | 376/160 |
| 3,943,362 A | * | 3/1976 | Peelman | G01V 5/102 |
| | | | | 376/163 |
| 4,078,174 A | | 3/1978 | Goldman | |
| 4,228,350 A | | 10/1980 | Paap et al. | |
| 4,388,529 A | | 6/1983 | Peelman | |
| 4,424,444 A | | 1/1984 | Smith, Jr. et al. | |
| 4,568,510 A | | 2/1986 | Caldwell | |
| 4,604,522 A | | 8/1986 | Arnold | |
| 4,697,078 A | | 9/1987 | Randall | |
| 5,025,150 A | | 6/1991 | Oldham et al. | |
| 5,237,594 A | | 8/1993 | Carroll | |
| 5,369,578 A | | 11/1994 | Roscoe et al. | |
| 5,410,575 A | * | 4/1995 | Uhm | G01V 5/234 |
| | | | | 376/160 |
| 5,539,225 A | | 7/1996 | Moriarty et al. | |
| 5,539,788 A | * | 7/1996 | Ruddy | G01N 23/222 |
| | | | | 376/160 |
| 5,781,602 A | | 7/1998 | Fero et al. | |
| 5,786,595 A | | 7/1998 | Herron et al. | |
| 6,026,135 A | | 2/2000 | Ing et al. | |
| 6,044,921 A | | 4/2000 | Lansberry | |
| 6,064,063 A | | 5/2000 | Mickael | |
| 6,124,590 A | | 9/2000 | Mickael | |
| 6,207,953 B1 | | 3/2001 | Wilson | |
| 6,577,697 B2 | * | 6/2003 | Pearcy | G21K 5/04 |
| | | | | 250/507.1 |
| 6,665,616 B2 | | 12/2003 | Mickael | |
| 6,703,606 B2 | | 3/2004 | Adolph | |
| 6,781,115 B2 | | 8/2004 | Stoller et al. | |
| 7,152,002 B2 | | 12/2006 | Lingren et al. | |
| 7,205,535 B2 | | 4/2007 | Madigan et al. | |
| 7,253,402 B2 | | 8/2007 | Gilchrist et al. | |
| 7,257,490 B2 | | 8/2007 | Georgi et al. | |
| 7,356,413 B2 | | 4/2008 | Georgi et al. | |
| 7,718,956 B2 | | 5/2010 | Ferguson | |
| 7,763,845 B2 | | 7/2010 | Estes et al. | |
| 7,880,134 B2 | | 2/2011 | Kirkwood et al. | |
| 8,269,162 B2 | | 9/2012 | Kirkwood et al. | |
| 8,286,857 B2 | | 10/2012 | Covely | |
| 8,338,777 B2 | | 12/2012 | Nikitin et al. | |
| 8,440,960 B2 | | 5/2013 | Oraby et al. | |
| 8,461,534 B1 | | 6/2013 | Koltick | |
| 8,476,584 B2 | | 7/2013 | Li et al. | |
| 8,604,442 B2 | | 12/2013 | Kraft et al. | |
| 8,642,944 B2 | | 2/2014 | Saenger et al. | |
| 9,086,500 B2 | | 7/2015 | Ansari et al. | |
| 9,274,245 B2 | | 3/2016 | Bliven et al. | |
| 10,209,392 B2 | * | 2/2019 | Vasquez | E21B 49/00 |
| 10,458,930 B2 | | 10/2019 | Torbert, III et al. | |
| 10,585,209 B2 | | 3/2020 | Inanc et al. | |
| 10,725,201 B2 | | 7/2020 | Mendez et al. | |
| 11,397,277 B2 | * | 7/2022 | Chin | G01N 23/222 |
| 2002/0150194 A1 | | 10/2002 | Wielopolski et al. | |
| 2017/0307550 A1 | | 10/2017 | Torbert, III et al. | |

OTHER PUBLICATIONS

Yakubova, G., et al. Benchmarking the Inelastic Neutron Scattering Soil Carbon Method. Vadose Zone Journal, 2016. 15: 1-11 vzj2015.04.0056. https://doi.org/10.2136/vzj2015.04.0056.

Yakubova et al., Measurements of Soil Carbon by Neutron-Gamma Analysis in Static and Scanning Modes. J. Vis. Exp. (126), e56270, doi:10.3791/56270 (2017).

Yakubova et al., Field Testing a Mobile Inelastic Neutron Scattering System to Measure Soil Carbon. Soil Sci 2014; 179: 529-535.

Kavetskiy et al., Scanning mode application of neutron-gamma analysis for soil carbon mapping. Pedosphere 2019; 29 (3): 334-343.

International Search Report and Written Opinion of the International Searching Authority for PCT/US2019/064950, mailed Apr. 22, 2020.

Jasmina Obhodas et al., Analysis of carbon soil content by using tagged neutron activation, Proc. SPIE 8371, Sensing Technologies for Global Health, Military Medicine, Disaster Response, and Environmental Monitoring II; and Biometric Technology for Human Identification IX, 83711B (May 4, 2012). (Year: 2012).

(2) Paulo E. Cruvinel et al., Studying the spatial variability of Cr in agricultural field using both particle induced X-ray emission (PIXE) and instrumental neutron activation analysis (INAA) technique, Nuclear Instruments and Methods in Physics Research B 109/110, pp. 247-251 (1996). (Year: 1996).

D. C. Glasgow et al., Methods for preparing comparative standards and field samples for neutron activation analysis of soil, Journal of radioanalytical and nuclear chemistry, vol. 192 (2), pp. 361-370 (1995). (Year: 1995).

Notice of Deficiencies for Israel Patent Application 283676, Jun. 25, 2023, 4 pages.

* cited by examiner

SCANNING MODE APPLICATION OF NEUTRON-INDUCED GAMMA ANALYSIS FOR SOIL CARBON MAPPING

CROSS-REFERENCE TO RELATED APPLICATIONS

This application claims the benefit of priority under 35 USC § 120 of U.S. application Ser. No. 16/706,013, filed on Dec. 6, 2019, (U.S. Pat. No. 11,397,277 issued on Jul. 26, 2022), which claims the benefit under 35 USC § 119(e) of U.S. Provisional Application Ser. No. 62/776,822, filed on Dec. 7, 2018. The disclosures of each of these applications are hereby incorporated in their entirety by reference herein.

GOVERNMENT RIGHTS

This invention was made with government support under Grant/Contract No. 2016-67021-24417 awarded by the National Institute of Food and Agriculture (NIFA), United States Department of Agriculture (USDA). The government has certain rights in the invention.

TECHNICAL FIELD

The present disclosure relates to systems and methods for mapping a distribution of at least one compound within soil.

BACKGROUND

Elemental content analysis of soil of a given geographic area may reveal whether the soil is adaptable to particular uses, such as agricultural, recreational, and so on. Other uses of soil content analysis include determining carbon credits and the level of availability of nutrients or the need for nutrient introduction to evaluate present and projected yields and potential profitability of fertilization.

Soil analysis may begin with soil sample collection, such that only a tiny portion of a field is actually analyzed in the laboratory. For example, one common method of soil elemental content analysis is composite sampling, where several subsamples of the soil are collected from randomly selected locations in the field. The subsamples are then mixed and the mixture analyzed for elemental content. In some instances, a quantity of a given element revealed to be contained within the mixture may be treated as an average quantity of that element within the entire area of the field being analyzed.

While an actual number of subsamples may vary slightly based on field size and uniformity, a number of subsamples usually does not exceed 20 and, at times, amounts to less than 0.01% of the acreage being analyzed. Moreover, most soil testing and analysis systems are not readily adaptable to test more than a few samples and, at best, provide a high-level approximation of a true elemental content of the soil of the field. Since the importance of accuracy of elemental content of the soil cannot be overstated, a methodology yielding more detailed and accurate elemental content information for a given field area is needed.

SUMMARY

A system for analyzing soil content of a field, the system includes a data acquisition unit configured to detect gamma spectra of each of a plurality of soil samples, wherein a surface area of the field is divided into a plurality of portions and the plurality of soil samples comprises at least one soil sample from each of the plurality of portions, a navigation unit configured to detect geographic coordinates of each of the plurality of soil samples, a data analysis unit configured to associate the detected gamma spectra of each of the plurality of soil samples with the geographic coordinates of the soil sample and determine a weight percent of at least one element within each of the soil samples based on the detected gamma spectra, and an element content map unit configured to generate a map indicating concentration of the at least one element within the soil of the field.

A method for analyzing content of soil of an agricultural field, the method includes dividing a surface area of the field into a plurality of portions, scanning at least one soil sample within each of the portions to detect gamma spectra of the soil sample, associating the detected spectra with a geographic location of the soil sample, calculating, based on the detected spectra, an amount of at least one element within the soil sample, and generating a map indicating the amount of the at least one element within each portion of the field.

A system for analyzing elemental content of soil of a field, the system includes a data acquisition unit configured to collect gamma spectra of at least one soil sample, a navigation unit configured to provide geographic coordinates of the soil sample, a data analysis unit configured to associate the collected gamma spectra with the geographic coordinates of the soil sample and calculate a weight percent of an element within the soil sample, and an element content map unit configured to generate a map indicating a concentration of the at least one element within the soil sample based on the calculated weight percent.

BRIEF DESCRIPTION OF THE DRAWINGS

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
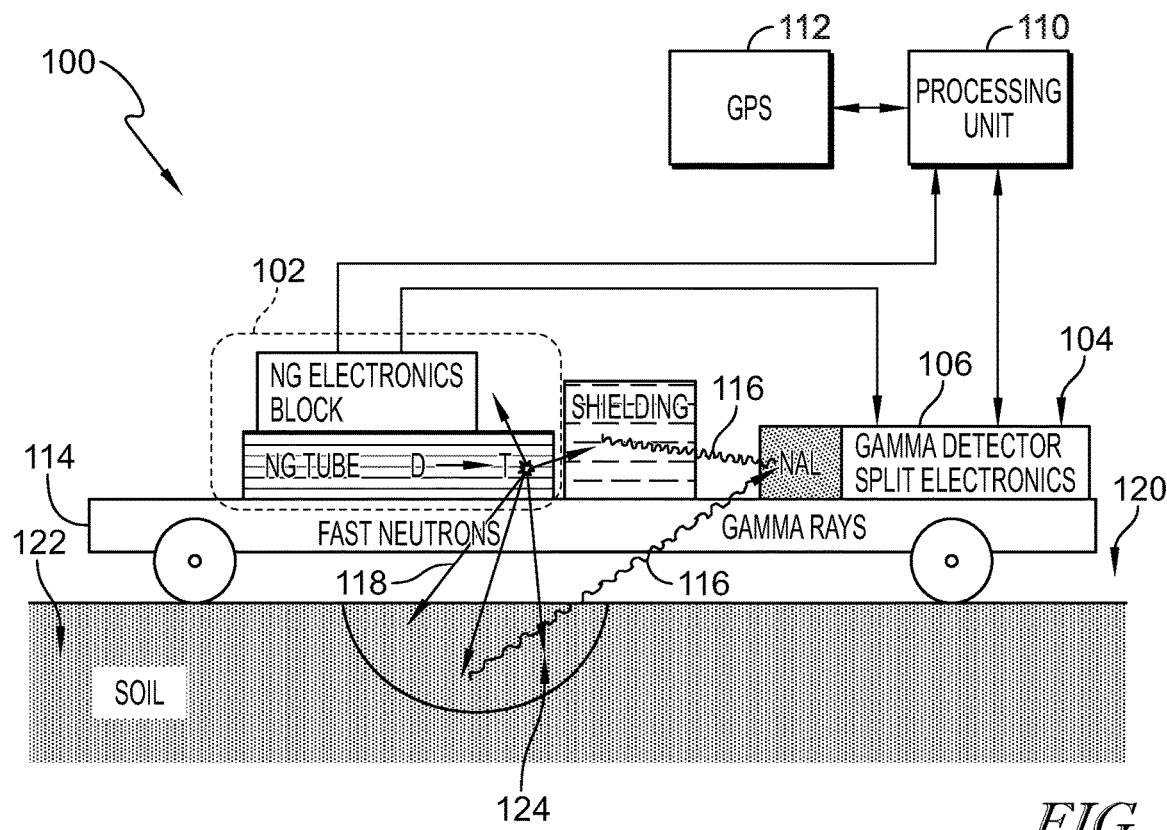
FIG. 1 is a simplified diagram illustrating an example implementation of a gamma analysis apparatus.

While the concepts of the present disclosure are susceptible to various modifications and alternative forms, specific embodiments thereof have been shown by way of example in the figures and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

The disclosed embodiments may be implemented, in some cases, in hardware, firmware, software, or any combination thereof. The disclosed embodiments may also be implemented as instructions carried by or stored on a transitory or non-transitory computer-readable storage medium, which may be read and executed by one or more processors. A computer-readable storage medium may be embodied as any storage device, mechanism, or other physical structure for storing or transmitting information in a form readable by a computing device (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

An example system for developing a detailed and accurate elemental content of soil of a given field may include a neutron generator device and a plurality of gamma detectors (e.g., sodium iodine gamma detectors) for scanning at least a portion of the field and a computing system for storing and analyzing the results of the scan and generating a map indicative of elemental content of the portion of the field. The example system may be a mobile system and may be configured to travel over a substantial portion of the field to perform the scan of the soil. According to some embodiments of the present disclosure, the elemental (C, Si, 0, H, K, Cl, and others) content in soil may be calculated using the measured spectra captured by the gamma detectors.

The example system may be further configured to communicate to a global positioning system (GPS) device to capture geographic location of the soil during the scanning process. In one example, the elemental content data identified during the scan may be combined (or associated) with geographic coordinates provided by the GPS device. Additionally or alternatively, based on the elemental content determined from the scan and the associated geographic coordinates, the example system may be configured to generate an element distribution map suitable for agricultural and other purposes.

FIG. 1 illustrates an example system 100 for analyzing soil samples 124 of a field 120. The system 100 may comprise one or more components for soil elemental analysis. In one example, the system 100 includes a neutron generator device 102, a plurality of gamma detectors 104, split electronics 106, and a processing unit (or processor) 110. While not separately illustrated, the example system 100 may include one or more additional or alternative components, such as, but not limited to, processing and memory/data store units and devices, audio and video scanning devices, and so on, configured to acquire, process, store, and/or analyze elemental analysis data. Additionally or alternatively, any neutron generator device 102 could be used, and this disclosure is not limited to a neutron generator device 102. Furthermore, accelerator-based neutron sources, such as deuterium-deuterium (D-D) and deuterium-tritium (D-T) fusion neutron generators and others that allow for electronic control of neutron emission 118 are preferred. The D-T neutron generators, in particular, may be preferred in practicing the present invention. Such generators may be pulsed (i.e., turned off and on for various lengths), providing electronic control of neutron emission 118.

The processing unit 110 may be configured to monitor and operate the neutron generator device 102, the plurality of gamma detectors 104, and the split electronics 106 to conduct scanning of the field 120 and analysis of the spectra data collected during the scan. The system 100 may be in communication with a global positioning system (GPS) device 112 to receive one or more geographic coordinates. In an example, the processing unit 110 may be configured to request geographic coordinates indicative of a geographic location of a soil sample 124. In another example, the processing unit 110 may associate the received geographic location of the soil sample 124 with data indicative of detected gamma spectra 116 of that soil sample 124.

Figure 2A:
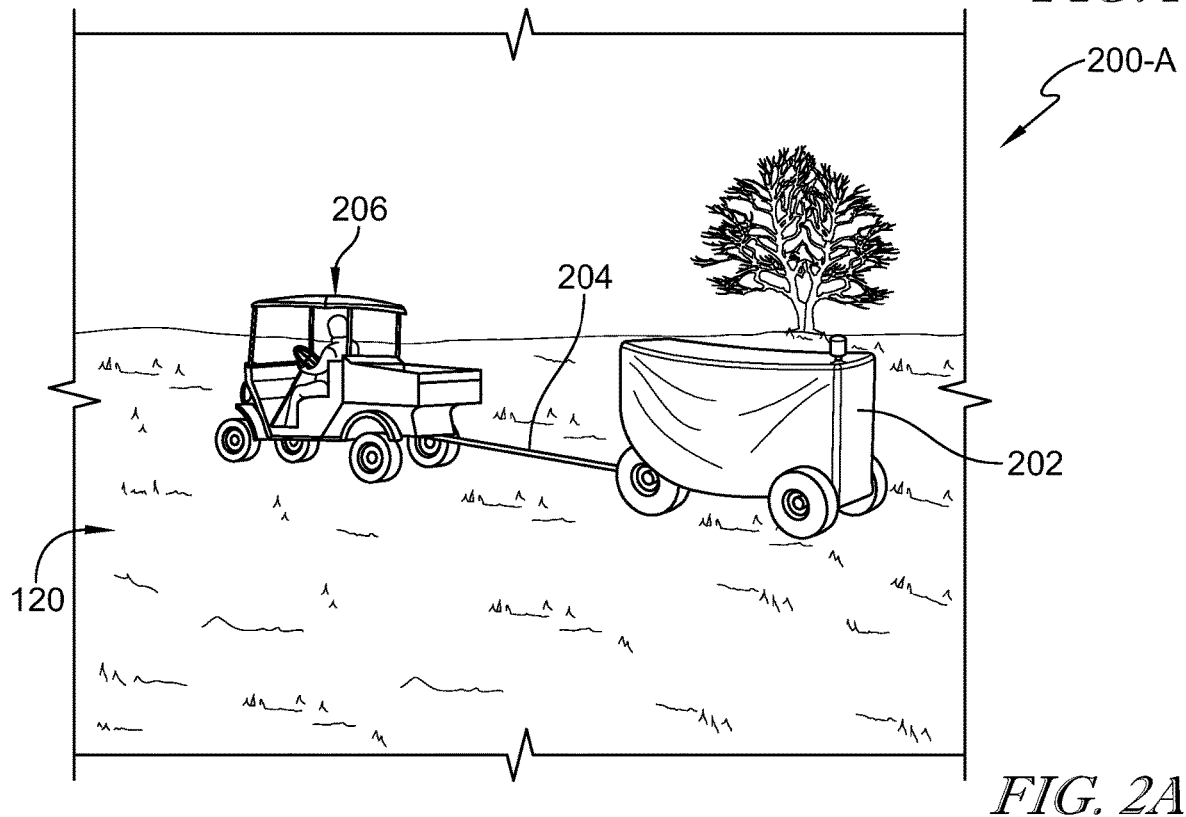
FIGS. 2A-2B are simplified diagrams illustrating example mobile implementations of the gamma analysis apparatus.
Figure 2B:
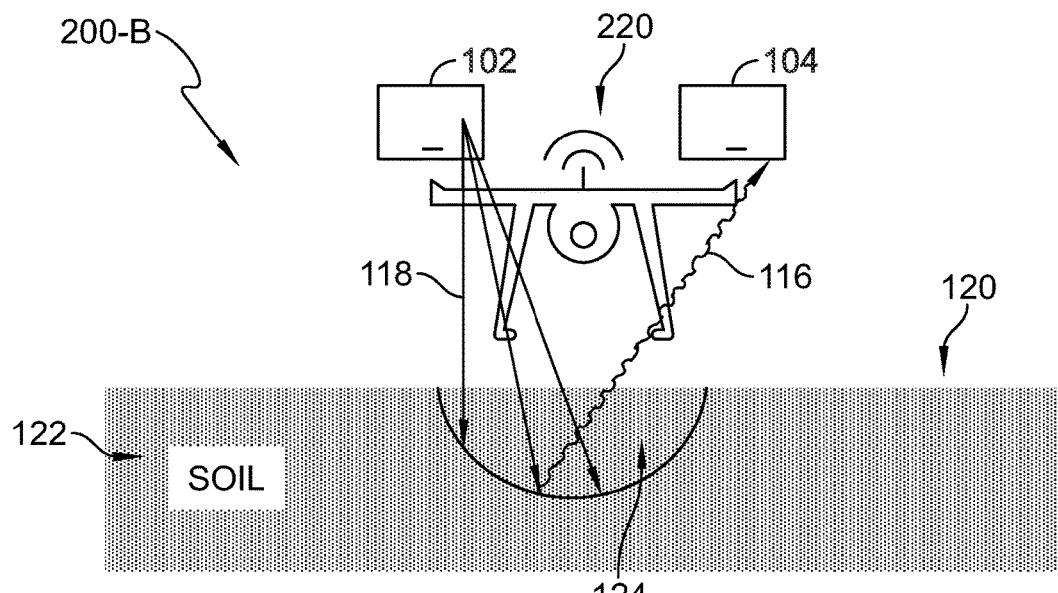

One or more components of the system 100 may be disposed on and/or secured to a fixture, a cart, or another rigid or semi-rigid structure 114. The structure 114 may be self-propelled, or driven directly or remotely, to travel over at least a portion of the field 120 to scan the soil 122. FIG. 2A illustrates an example mobile implementation 200-A of the soil analysis system 100, wherein at least a portion of the system 100 is disposed in a trailer 202. The trailer 202 may be pulled 204 across the field 120 by a motorized vehicle 206, whether gas- or battery-powered. Additionally or alternatively, FIG. 2B illustrates an example mobile implementation 200-B of the system 100, wherein one or more components of the system 100 are disposed on and/or secured to a remote-controlled pilotless aircraft, such as a drone 220.

FIGS. 3-15 illustrate example processes performed by the system 100 to scan soil of the field 120, analyze and store scanned data corresponding to the soil 122 of the field 120, and to generate an elemental content map of the field 120 based on the spectral data acquired during the scan. One or more processes, such as, but not limited to, analyses, computations, and map generation tasks may be performed by the processing unit 110. Additionally or alternatively, scan data collected by one or more components of the system 110 during the scan may be downloaded or otherwise extracted from the system 100 and exported for further processing on a remote (e.g., cloud-based) computing system. Other scan data collection, processing, and analysis methods are also contemplated.

Figure 3:
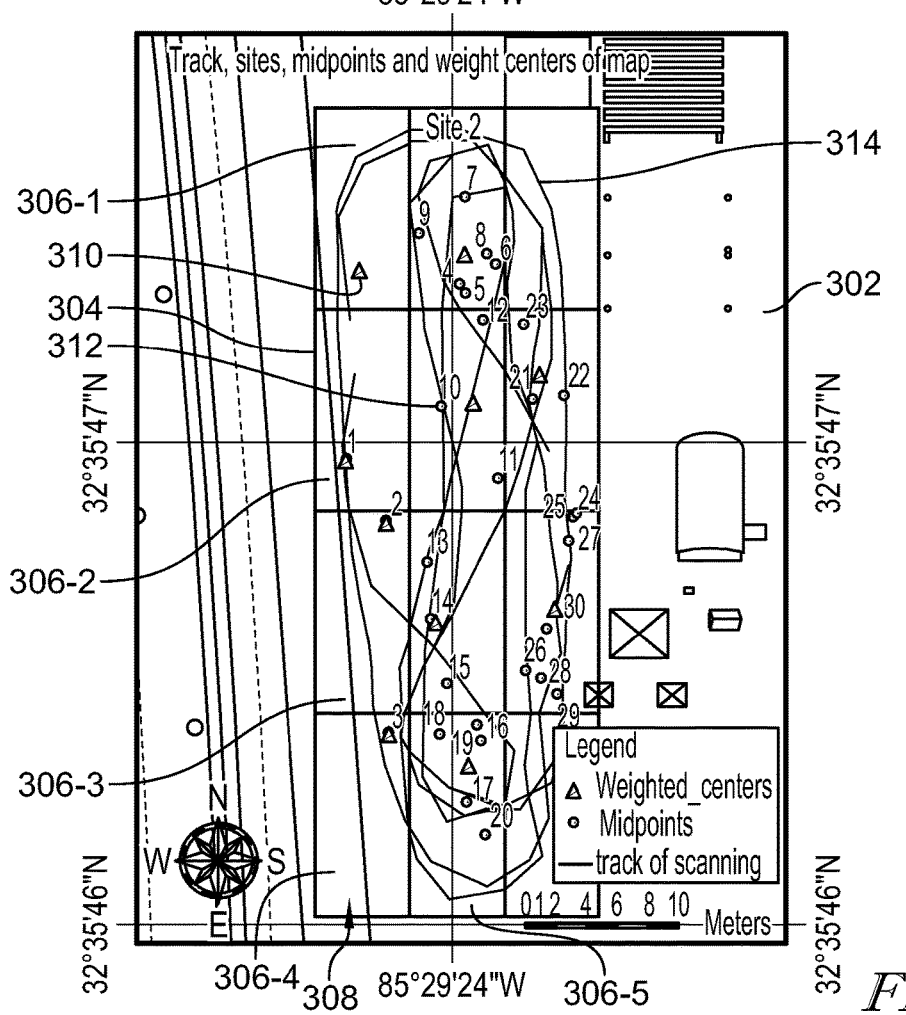
FIG. 3 is a simplified diagram illustrating a plurality of portions of a field to be scanned by the gamma analysis apparatus.

FIG. 3 illustrates an example diagram 300 of an area 302 to be scanned by the soil analysis system 100. In one example, the processing unit 110 of the system 100 may be configured to divide the field 120 into a plurality of portions (blocks, or sites) 306 prior to initiating the scanning operation. In some instances, the number of portions (hereinafter, sites) 306 may be based on the field size and presence of one or more landscape features. For example, when determining the sizes of the sites 306, the appropriate speed for scanning (e.g., ~5 km/h) and the terrain profile may be considered. Each site 306 may comprise a relatively homogeneous terrain profile. During field division, the processing unit 110 of the system 100 may be configured to designate a separate site 306 in response to detecting a change in terrain type, such as an asphalt road 308 crossing the field 120 and so on, and/or detecting a change in a profile and make-up of the terrain, e.g., in response to detecting a low spot in the terrain. Given the aforementioned terrain-related and other factors affecting scanning conditions, each site 306 of the plurality of sites 306 may vary in size from less than ~100 m² to ~1000 m² and greater. In the example illustrated in FIG. 3, a total area of the field 120 was approximately 800 m² and a number of sites was 12.

The processing unit 110 of the system 100 may be configured to scan the soil 122 for a predefined period of time in order to achieve a predefined desired accuracy value in identifying a presence or absence of a given element within the soil 122 of the site 306 and/or in measuring an amount of the element within the soil 122 of the site 306. In some instances, a period of time for which the processing unit 110 of the system 100 scans each site 306 may be based on a gamma peak yield of the element, that, in turn, may be affected by an amount of that element within the soil of the site 306, a chemical, molecular, and/or anatomic structure of the element being identified, and one or more other characteristics.

Additionally or alternatively, the period of time for which to scan each site 306 based on a predefined desired accuracy value of the measurement. For instance, to reach an accuracy of ±0.5 w % for carbon content measurements, the acquisition time for one site may be 15 min. As another example, the system 100 measurement time for silicon with an acceptable accuracy of ±0.5-1 w % may be ~5 min, due to silicon gamma peak yield for silicon being several times greater than carbon peak yield (due to its higher content in soil 122).

The system 100 may be configured to identify a geographic position, e.g., geographic coordinates, of each of the plurality of sites 306 and to mark and number each site 306 on a digital rendering of a map. In one example, the processing unit 110 of the system 100 may be configured to request and receive the geographic coordinates of each site 306 from the GPS unit 112 (internal or external to the system 100) with which the system 100 communicates using, for example, a wired network connection, another type of network communication medium, or a long-range or a short-range wireless network, such as, but not limited to wireless local area network (LAN), Bluetooth, wide area network (WAN), and so on. Accordingly, the processing unit 110 of the system 100 may be configured to acquire and track a current geographic position of the system 100 with respect to the ongoing path are displayed over a map of the sampling field at runtime.

During the scanning operation, the system may determine, for each individual site 306, a period of time during which gamma spectra of the soil 122 has been scanned for the site 306. The processing unit 110 of the system 100 may be configured to alter a color of a given site 306 on the displayed map responsive to a period of time during which the soil 122 of that site 306 has been scanned. In some instances, the system may change or alter a color of the site 306 on the displayed map based on a total acquisition time collected within each site 306 during the scan runtime. In one example, the processing unit 110 of the system 100 may use color-coding to indicate that a predefined sufficient amount of data has been acquired for accurate soil element determination for that site 306, such as when all of the sites 306 have turned a predefined color, the processing unit 110 may issue a corresponding command and/or notification indicating that the scanning operation has been completed.

The INS and TNC spectra from each detector 104 acquired during the scanning are displayed on the laptop screen at runtime. The processor 110 may be configured to store at predefined periods, e.g., every 30 s, the gamma spectra (the INS and TNC spectra from each of the gamma detectors 104) of the soil 122 of a given site 306 and the corresponding geographical coordinates of that site 306. The system 100 may be configured to regularly check whether a connection is maintained between the GPS device 112 and the processing unit 110 and/or memory in the recording equipment. Further, in response to detecting that the connection between the GPS device and the recording equipment has been lost, the system 100 may be configured to issue a corresponding alert and may pause the recording of the scanning data to prevent inaccurate data from being recorded. In some instances, a total number of saved spectra may reach several thousand or more depending on the scanning time. After scanning, the saved spectra may be transferred to one or more data processing component (not shown) of the system 100.

At the beginning, the net INS spectra for every 30 s measurement are calculated.

The net INS spectra (netINS$_{r,i}$) in counts per second (cps) per channel for each r-th record and each i-th detector 104 may be calculated using Equation (1), such that $$netINS_{r,i} = \frac{INS_{r,i} - INS_{r-1,i}}{LT_{INS,r,i} - LT_{INS,r-1,i}} - \frac{TNC_{r,i} - TNC_{r-1,i}}{LT_{TNC,r,i} - LT_{TNC,r-1,i}} \quad (1)$$

where LT$_{INS,r,i}$ and LT$_{TNC,r,i}$ are indicative of a lifetime of r-th record and i-th detector 104, respectively, and where INS$_{r,i}$ and TNC$_{r,i}$ are indicative of a measured spectra of r-th record and i-th detector 104, respectively. Following this, all subsequent actions with spectra may be performed channel by channel.

Lifetime (LT) may be calculated using Equation (2), such that $$LT = RT \cdot \frac{OCR}{ICR}, \quad (2)$$

where RT is indicative of a real measurement time in seconds (s), OCR is indicative of an output count rate, and ICR is indicative of an input count rate. In some instances, RT, OCR, and ICR parameters may be defined by specifications of a spectra acquisition hardware used to perform the scanning operation. Moreover, RT, OCR, and ICR parameter values may be included in each corresponding spectrum file.

In an example, each detector 104 may comprise a unique energetic calibration indicative of a dependence between energy and a channel number. A change in environmental conditions present on a given day or time of the scan may cause the dependence to change. To bring all spectra to one energetic calibration, the spectra may be shifted such that centroids of dominant peaks (e.g., silicon and oxygen peaks) are in the same channels in all spectra.

After shifting, the eight $netINS_{r,i}$ spectra may be summarized channel by channel, and the net INS spectrum ($netINS_r$) for each r-th record can be calculated using Equation (3), such that $$netINS_r = \Sigma_3 netINS_{r,i} \quad (3)$$

The lifetime for that spectrum ($\Delta LT_{avg,r}$) may be defined as an average of corresponding lifetimes of each of the plurality of detectors 104, such that $$\Delta LT_{avg,r} = \frac{\Sigma_3 (LT_{INS,r,i} - LT_{INS,r-1,i})}{3} \quad (4)$$

The $netINS_r$ spectra with $\Delta LT_{avg,r}$ are attributed to the position of the geographical midpoint 312 between two adjacent records. Thus, the data set $netINS_r$ spectra, $\Delta LT_{avg,r}$ and geographical coordinates of middle points are generated, as illustrated in FIG. 3.

Further with reference to FIG. 3, the data with midpoint 312 coordinates may be sorted by sites 306, such that, for example, the midpoints 312 identified using numbers 4, 5, 6, 7, 8, and 9 are attributed to Site #2 and so on. The weighted centers 310 for a given site 306-n may be determined based on the midpoints 312 attributed to that site 306-n. The average $netINS_S$ spectra of a site S, in cps per channel, may be determined using Equation (5), such that $$netINS_S = \frac{\Sigma_{all\ r\ in\ this\ site}\ netINS_\gamma \cdot \Delta LT_{avg,r}}{\Sigma_{all\ r\ in\ tis\ site} \Delta LT_{avgr}} \quad (5)$$

Accordingly, the average $netINS_S$ spectra of each site 306 may be used to determine an elemental content of each of the plurality of sites 306. The element content may be calculated from the corresponding element (nuclei) gamma peak area. The peak area may be calculated from the $netINS_S$ spectra by the designed software using IGOR software. In some instances, element content distribution may be calculated based on previously defined calibration data or other parameters or values.

As discussed further in reference to at least FIGS. 8-15, elemental distribution maps for carbon, silicon, hydrogen and potassium may be plotted based on data collected during a scanning operation. The carbon and silicon content distribution may be defined from the $netINS_S$ spectra. Further, TNC spectra data may be used for determining hydrogen content. Potassium content and mapping may be determined based on the natural gamma background spectra measurements.

Equation (6) may be used to determine a carbon content (in weight percent, Cw %), such that $$Cw\ \% = \frac{(PA_{4.44} - PA_{4.44,bkg}) - 0.0496 \cdot (PA_{1.78} - PA_{1.78,bkg})}{13.733}, \quad (6)$$

where $PA_{4.44}$, $PA_{1.78}$, $PA_{4.44,bkg}$=140 cps, $PA_{1.78,bkg}$=453 cps are indicative of the peak area with a centroid 4.44 MeV (carbon peak) and the peak area with the centroid 1.78 MeV (the silicon peak) in the $netINS_s$, and the system background in the gamma spectra of 0.0496 and 13.733 are indicative of the respective calibration coefficients.

Figures 4A, 4B:
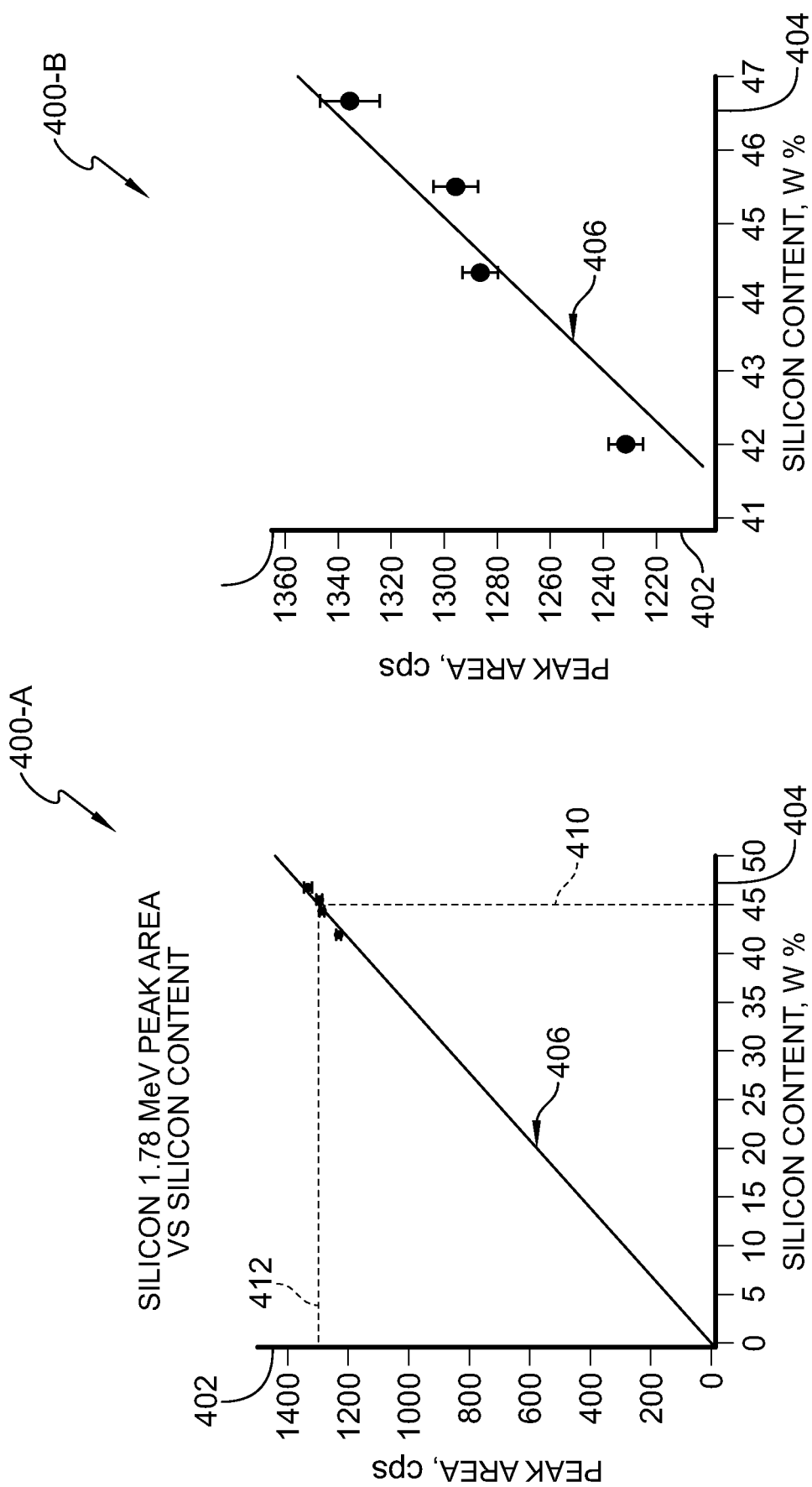
FIG. 4A is a graph illustrating an example relationship between a peak area and a weight percent of silicon.
FIG. 4B is a graph illustrating a portion of the graph illustrated in FIG. 4A.

FIG. 4 illustrates an example diagram 400 for determining elemental content of silicon based on the calibration dependence. For example, a reasonable approximation of a silicon calibration dependence may be determine based on several points, e.g., four (4) data points and a zero-zero point. In some instances, additional scan data may be used to continue improving the silicon calibration.

Accordingly, the silicon content may be determined based on Equation (7), such that $$Siw\ \% = \frac{(PA_{1.78} - PA_{1.78,bkg})}{28.834}. \quad (7)$$

The soil hydrogen distribution may be determined based on the hydrogen peak area in the TNC spectra, with centroid peak of 2.223 MeV. In one example, to define the hydrogen peak area, the TNC spectra for r-th record and i-th detector 104 may be calculated on a channel-by-channel basis using Equation (8), such that $$\Delta TNC_{r,i} = \frac{TNC_{r,i} - TNC_{r-1,i}}{LT_{TNC,r,i} - LT_{TNC,r-1,i}} \quad (8)$$

The shifting, summarizing spectra over a plurality of gamma detectors 104, determining the average life time and midpoint 312 geographical position, sorting spectra by sites 306, determining the weighted centers 310 of sites 306 and average TNC spectra for site 306 may be determined in a manner similar to that of the netINS spectra determination. Specifically, $$\Delta TNC_r = \Sigma_3 \Delta TNC_{r,i} \quad (9)$$

$$\Delta LT_{avgTNC,r} = \frac{\Sigma_3 (LT_{TNC,r,i} - LT_{TNC,r-1,i})}{3} \quad (10)$$

$$\Delta TNC_S = \frac{\Sigma_{all\ r\ in\ this\ site} \Delta TNC_r \times \Delta LT_{avgTNC,r}}{\Sigma_{all\ r\ in\ this\ site} \Delta LT_{avgTNC,r}} \quad (11)$$

Further, spectra the peak areas of hydrogen may be calculated from the $TNC_s$ and the value of the hydrogen peak area and weighted centers in the sites may be used to plot the hydrogen distribution map.

The soil potassium distribution map may be generated in a manner similar to the process outlined with respect to other elements analyzed by neutron-gamma technology, e.g., by the neutron pulse source 102 and/or the gamma detectors 104 and associated components of the system 100, such as hydrogen and silicon. Additionally or alternatively, potassium content may be determined based strictly on the natural gamma spectra collected from the soil and without relying on neutron irradiation of the soil. For example, the $^{40}$K isotope may be naturally present within the potassium isotopes mixtures of potassium containing compounds. This isotope has a known abundance in potassium compounds of n=0.0117% and it is radioactive ($T_{1/2}$=1.248·10$^9$ years). The radioactive decay of $^{40}$K is accompanied by gamma ray emissions with energy 1.46 MeV, a gamma radiation that is one of the main components of natural radioactivity. Therefore, potassium presence in soil may be determined based on measured gamma line intensity.

Figure 5:
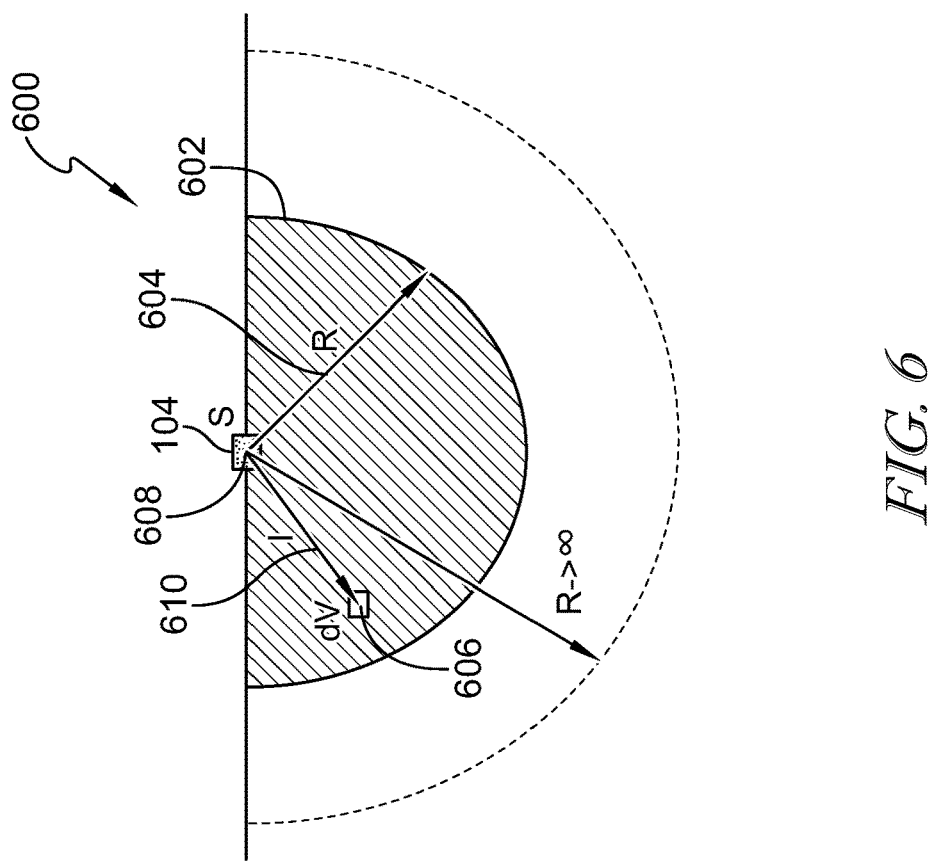
FIG. 5 is a graph illustrating an example relationship between a gamma analysis yield and energy of potassium.

FIG. 5 illustrates an example graph 500 of the gamma spectrum of natural radioactivity and may be indicative of the spectrum measured during 0.5 hour by the system 100 installed directly on the soil 122 surface. In one example, the dashed line 506 may be indicative of the gamma spectrum measured when a potassium containing substance (~11 kg) (total weight 22.7 kg) was placed under the measurement system, where a significant peak (such as between energy values 508-1 and 508-2) with centroid at or about 1.46 MeV indicates a presence of potassium.

Figure 6:
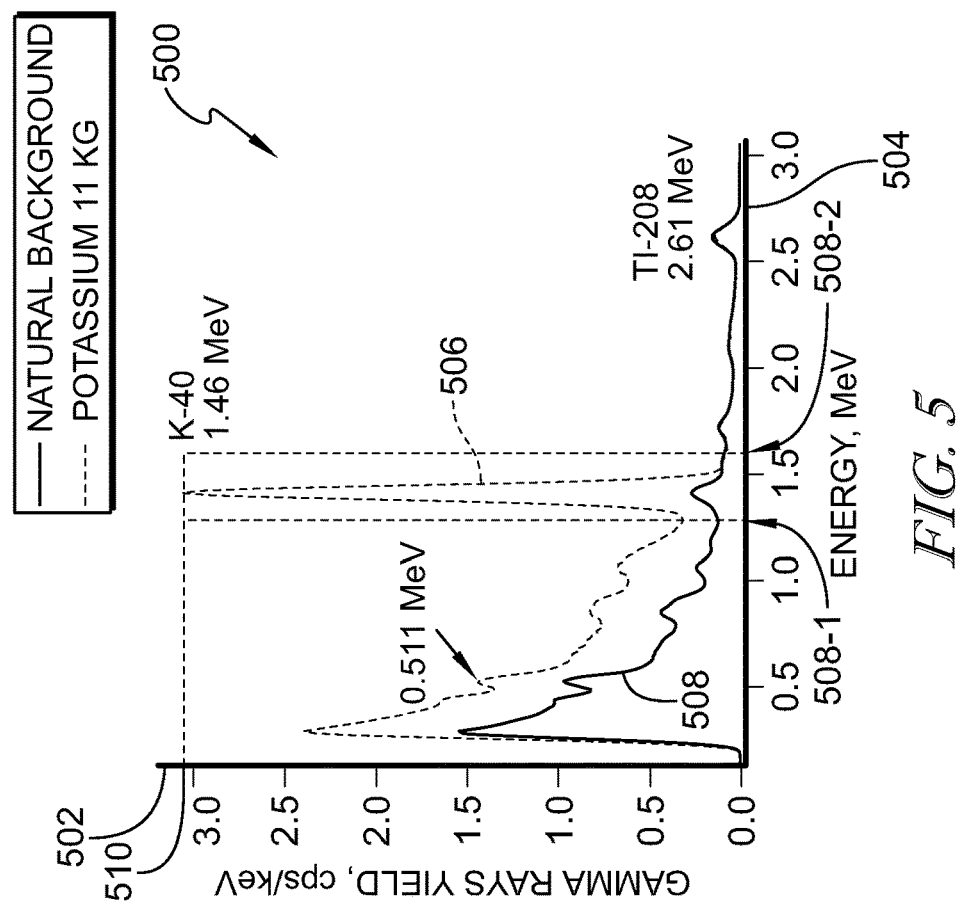
FIG. 6 is a simplified diagram illustrating an example methodology for determining potassium content of the soil.

FIG. 6 illustrates an example diagram 600 of a methodology for estimating a potassium calibration coefficient. For the first approximation, soil potassium was assumed to be uniformly distributed in hemispherical volume with radii R. The gamma detector 104 was situated at the center 608 of this hemisphere 602. If Kw % 606 was present in the unit volume dV 606, and material density is d, then dy, s$^{-1}$, gamma rays with energy 1.46 MeV would appear as $$d\gamma = \frac{Kw\ \%}{100} \cdot d \cdot \eta \cdot \frac{N_A}{AW} \cdot \lambda \cdot dV \quad (12)$$

where $N_A$ is Avogadro number and A W is an atomic weight of potassium, $\lambda$=0.693/$T_{1/2}$. Then the signal intensity of gamma detector 104 (peak area, S) can be calculated as $$S = t \cdot \eta \cdot \frac{N_A}{AW} \cdot \lambda \cdot G \quad (13)$$

$$G = \frac{Kw\ \%}{100} \cdot d \int_0^{2\pi} \int_0^{\pi/2} \int_0^R \frac{\exp(-\mu \cdot d \cdot l)}{4\pi l^2} \cdot dV = \quad (14)$$

$$\frac{Kw\ \%}{100} \cdot d \int_0^{2\pi} \int_0^{\frac{\pi}{2}} \int_0^R \frac{\exp(-\mu \cdot d \cdot l)}{4\pi} \cdot \sin\theta dl d\theta d\varphi$$

where t is gamma ray registration efficiency, µ is mass adsorption coefficient of 1.46 MeV gamma line in substance, distance l is a distance between dV and gamma detector 104, and R is hemisphere radii. Kw % in potassium containing substance is 11/22.7·100%=48.4%. The bulk density of this substance was 1.1 g cm$^{-3}$, and the radii of hemisphere with this substance is $$\sqrt[3]{\frac{22700 \cdot 3}{d \cdot 2\pi}} = 21.4\ cm.$$

Mass attenuation coefficient for potassium containing substance (KCl) for 1.6 MeV is 0.048 cm$^2$ g$^{-1}$ and the value $G_{st}$=3.416. Peak area in spectrum was calculated as 237 cps for potassium containing substance, as illustrated by a dashed line in FIG. 5. From here, t value can be estimated as 69.4.

Soil density can be taken to be equal to 1.2 g cm$^{-3}$ and µ=0.052 cm$^2$ g$^{-1}$ (main soil elements are Si and O) for estimation. Then, for soil of infinity radii $G_{soil}$=Kw %/100·9.615, and potassium peak area was 14 cps for soil, as illustrated by a solid line in FIG. 5. Peak area is proportional to G and gamma ray registration efficiency t. From these values, the calibration coefficient for potassium in soil can be estimated as 0.15 Kw %/cps, and Kw % in soil can be estimated as 2%. This value agrees with average potassium content in soil. While this calibration should be repeated with several reference samples for better accuracy, an estimation of Equation (15) may be used for a given series of measurements, such that $$Kw\ \% = 0.15 \cdot PA_{1.46}. \quad (15)$$

The measured data sets of geographical coordinates and element contents (in weight %) were used to create element distribution maps. The map may be generated using a local polynomial interpolation or another computational approach. The map was put on the geographical base map. The generated elemental distribution map may include an arrow or another type of icon indicative of one or more cardinal directions, such as north, south, east, and west, to indicate directional orientation of the map. In other examples, the generated elemental distribution map may be automatically oriented such that an upward vertical direction signifies northward direction and so on. In some instances, the generated map may include a corresponding legend and/or a scale bar indicating one or more ranges of elemental content of a given element or a plurality of elements. The generated elemental distribution map may comprise a contour map including one or more contour value labels indicating regions with the same content. Some examples of elemental distribution maps generated based on gamma spectrum data analysis are illustrated in at least FIGS. 8-15.

A first scanned field comprises a first total area, e.g., ~6 hectares (ha), and a second scanned field comprises a second total area, e.g., ~23 ha, with a soil type of Marvyn loamy sand and Marlboro loamy sand (1-6% slope), respectively.

Figure 7:
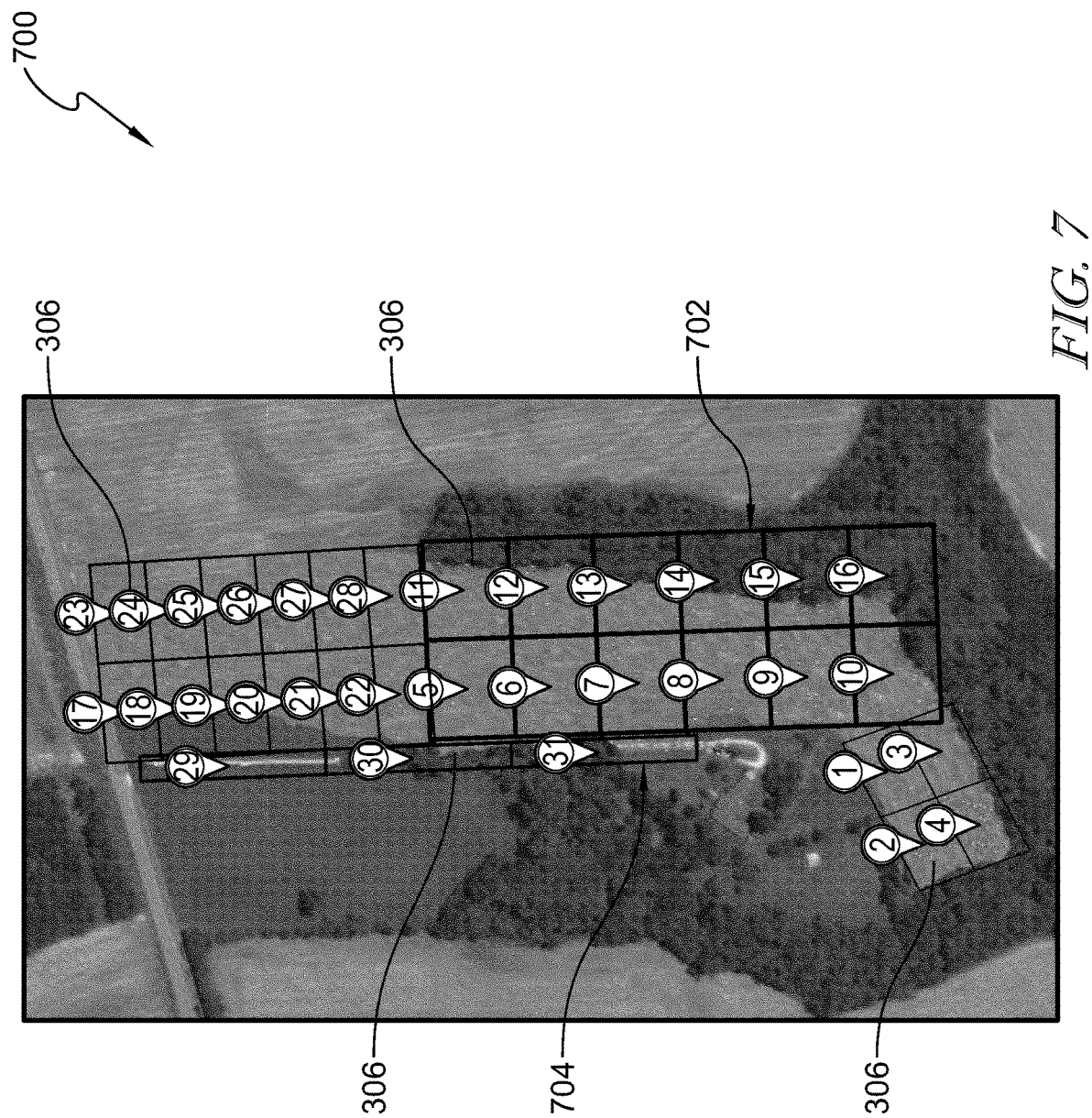
FIG. 7 is a simplified diagram illustrating a plurality of portions of a first scanned field.

FIG. 7 illustrates an example diagram 700 of a first scanned field 702 being divided into a plurality of sites 306, where a first plurality of sites 306 are situated on the first scanned field 702 and a plurality of sites 704 being on a road adjacent to the first scanned field 702. As one example, a number of midpoints in each site 306 and a total measurement time in each site 306 are shown in Table 1.

| Cell ID | Mid-points | Measurement time (min) |
|---|---|---|
| 1 | 34 | 17 |
| 2 | 17 | 8.5 |
| 3 | 31 | 15.5 |
| 4 | 16 | 8 |
| 5 | 30 | 15 |
| 6 | 23 | 11.5 |
| 7 | 16 | 8 |
| 8 | 24 | 12 |
| 9 | 24 | 12 |
| 10 | 27 | 13.5 |
| 11 | 22 | 11 |
| 12 | 20 | 10 |

-continued

| Cell ID | Mid-points | Measurement time (min) |
|---------|------------|------------------------|
| 13 | 18 | 9 |
| 14 | 15 | 7.5 |
| 15 | 22 | 11 |
| 16 | 7 | 3.5 |
| 17 | 10 | 5 |
| 18 | 25 | 12.5 |
| 19 | 19 | 9.5 |
| 20 | 19 | 9.5 |
| 21 | 24 | 12 |
| 22 | 19 | 9.5 |
| 23 | 19 | 9.5 |
| 24 | 16 | 8 |
| 25 | 21 | 10.5 |
| 26 | 16 | 8 |
| 27 | 19 | 9.5 |
| 28 | 16 | 8 |
| Road | | |
| 29 | 38 | 19 |
| 30 | 38 | 19 |
| 31 | 34 | 17 |

Figures 8, 9:
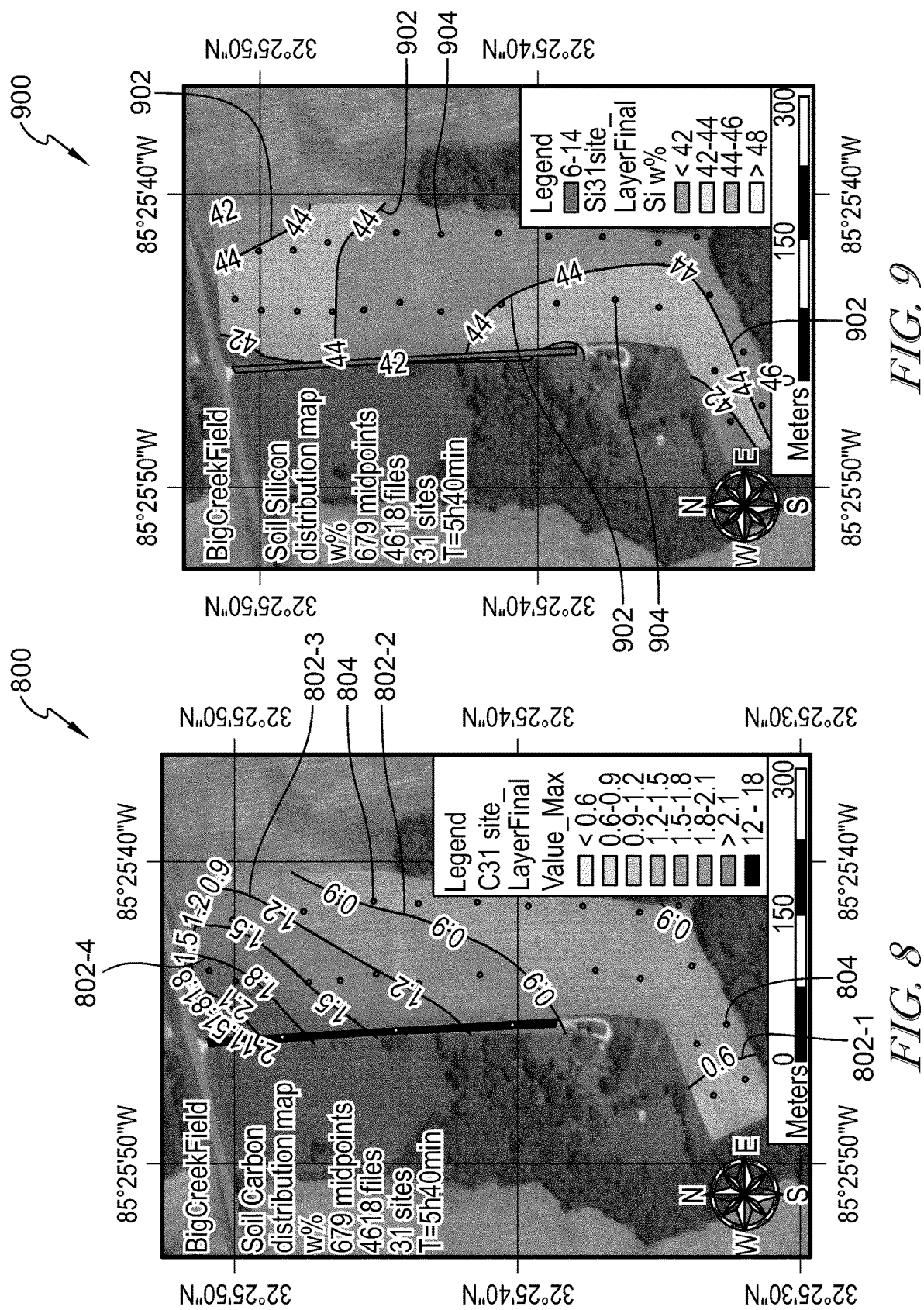
FIG. 8 is a simplified diagram illustrating a map of carbon distribution of the first scanned field.
FIG. 9 is a simplified diagram illustrating a map of silicon distribution of the first scanned field.

FIG. 8 illustrates an example diagram 800 of a digital rendering of a carbon distribution map 808 for the first scanned field 702 described in reference to at least FIG. 7. In one example, the carbon content distribution 802 increased from south to north (as illustrated, for example, by reference elements 802-1 through 802-4) from 0.5 to 2.0 w %, while the carbon content on the road was extremely high compared to the field 122, reaching 18 w %. FIG. 9 illustrates an example diagram 900 of a digital rendering of a silicon distribution map 908 for the first scanned field 702 described in reference to at least FIG. 7. In one example, silicon content distribution 902 on the first scanned field 702 varied, such that silicon content generally remained within a range of 44±2 w %. In another example, silicon content 902 was very low (around 10 w %) on the road adjacent to the field 702, meaning the road may have consisted of a mineral such as carbonate gravel and had very little silicon.

Figures 10, 11:
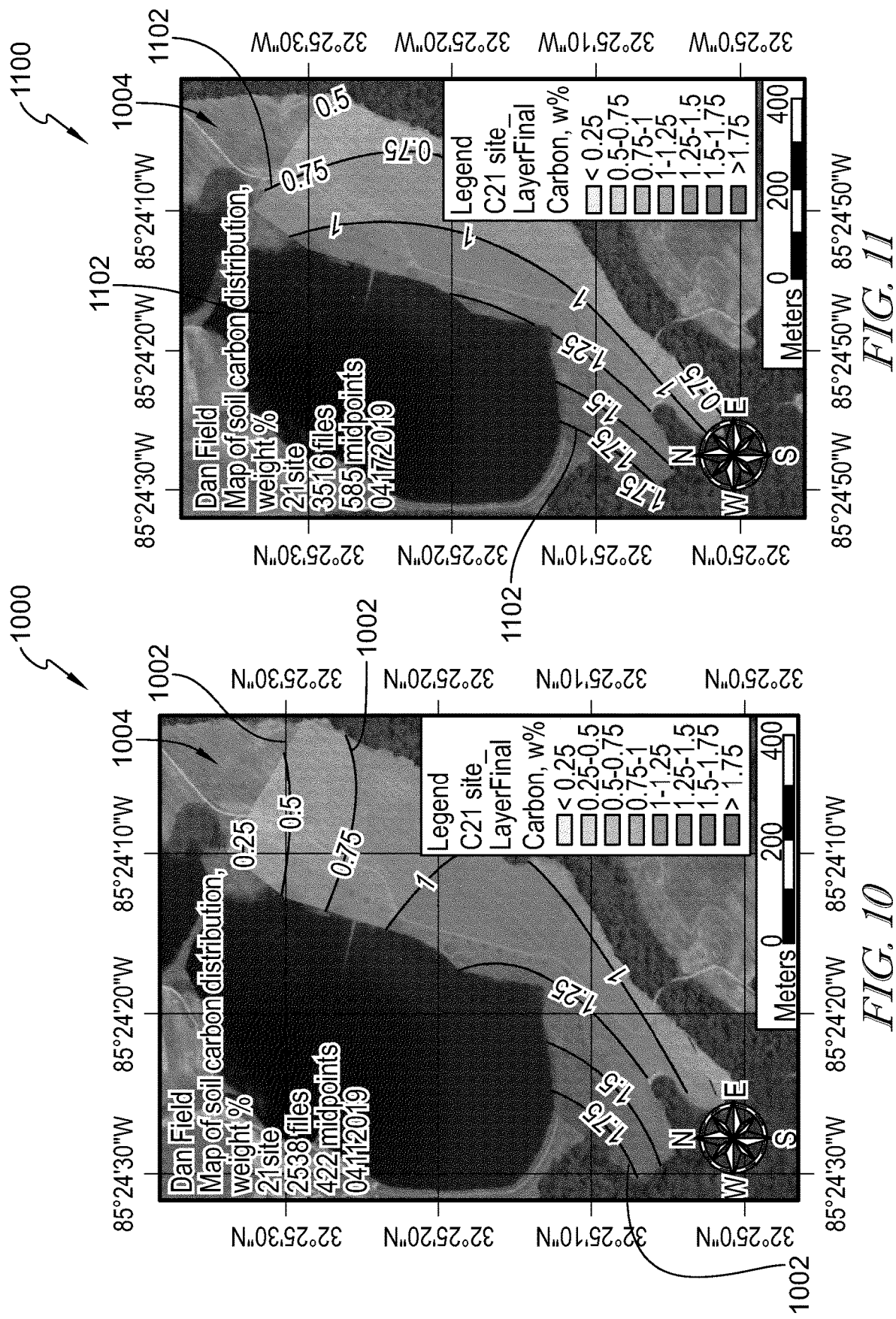
FIGS. 10 and 11 are simplified diagrams illustrating maps generated from scan operations of a second scanned field performed on two different days.
Figures 12, 13:
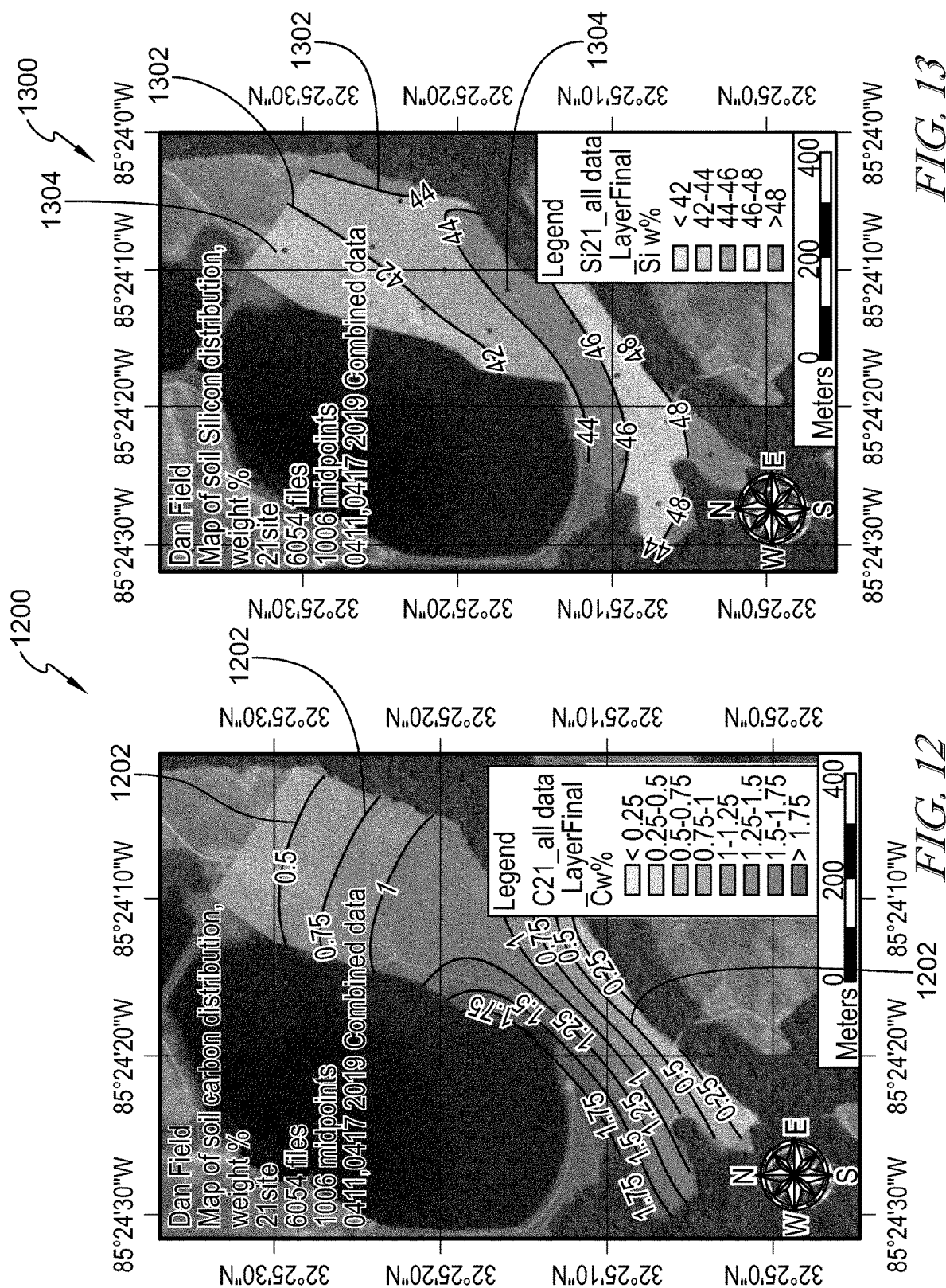
FIG. 12 is a simplified diagram illustrating a map of carbon distribution based on a combination of scan data of FIGS. 10 and 11.
FIG. 13 is a simplified diagram illustrating a map of silicon distribution of the second scanned field.

FIGS. 10 and 11 illustrate example maps 1000 and 1100, respectively, of the carbon distribution 1002, 1102 on a second scanned field 1004 captured on two different days, such as on Apr. 11, 2019 and Apr. 17, 2019 with the weather between the two dates being stable (sunny), where an area of the second scanned field 1004 is approximately 13.6 ha. The comparison demonstrates that both maps are quite similar, with some minor discrepancies in the contours 1002, 1102 being limited to respective northern portions of the maps 1000 and 1100. Thus, multiple scans of the second scanned field 1004 confirmed that the results of scans and the maps generated from the collected scan data remain relatively consistent under approximately the same weather conditions. Accordingly, the methodology and approach for using the gamma analysis apparatus system 100 to gather scan data of the soil 122 and generate elemental content distribution maps of the soil 122 based on the collected scan data is sufficiently accurate and the results of the methodology are reproducible under similar basic conditions. FIG. 12 illustrates a map 1200 indicative of elemental distribution 1202 of carbon (C) resulting from a combination of data sets 1000, 1100 used to generate maps of FIGS. 10 and 11 and may be a more reliable elemental content map. FIG. 13 illustrates silicon distribution map 1300 indicative of silicon elemental distribution 1302 based on a combined data of scanned operations of the second scanned field 1004 performed on two different days (not separately illustrated herein).

Figures 14, 15:
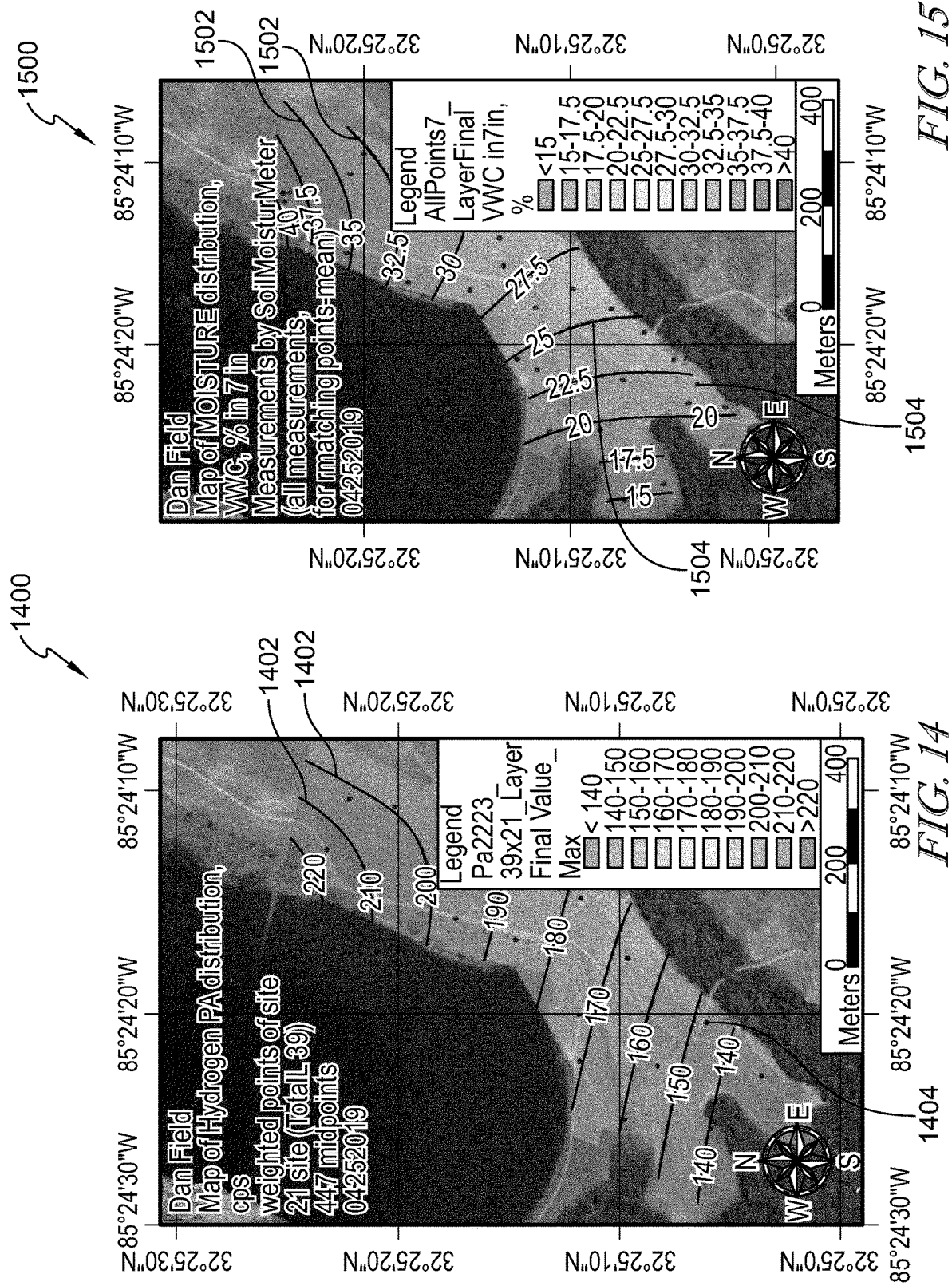
FIGS. 14 and 15 are simplified diagrams illustrating, respectively, a first map generated using methods of the present disclosure and a second map generated based on moisture measurements performed simultaneously with the first map.

FIG. 14 illustrates an example map 1400 of elemental distribution 1402 of hydrogen in the soil 122 of the second scanned field 1004. In one example, the hydrogen distribution map 1400 refers to a distribution of hydrogen peak areas, where element number 1404 is indicative of the respective peak values of each of the sites 306. FIG. 15 illustrates an example map 1500 generated from hydrogen scanning performed using moisture measurements using a TDR-300 Soil Moisture Meter. The length of electrodes was 7 inches (in), and "Sand" was selected as Soil Type mode during the measurement. The map 1500 of soil moisture measured by this instrument. A relative error of moisture measurement 1502 by TDR-300 (including corresponding peak values 1504) ranged between approximately 12% and 20%. Despite this relative error value of the moisture determination by TDR 300, the comparison of the maps 1400 and 1500 of the FIGS. 14 and 15, respectively, demonstrated the similarity between the two instruments and it may be concluded that using neutron gamma analysis for moisture distribution mapping 1402 may yield accurate results.

Figure 16A:
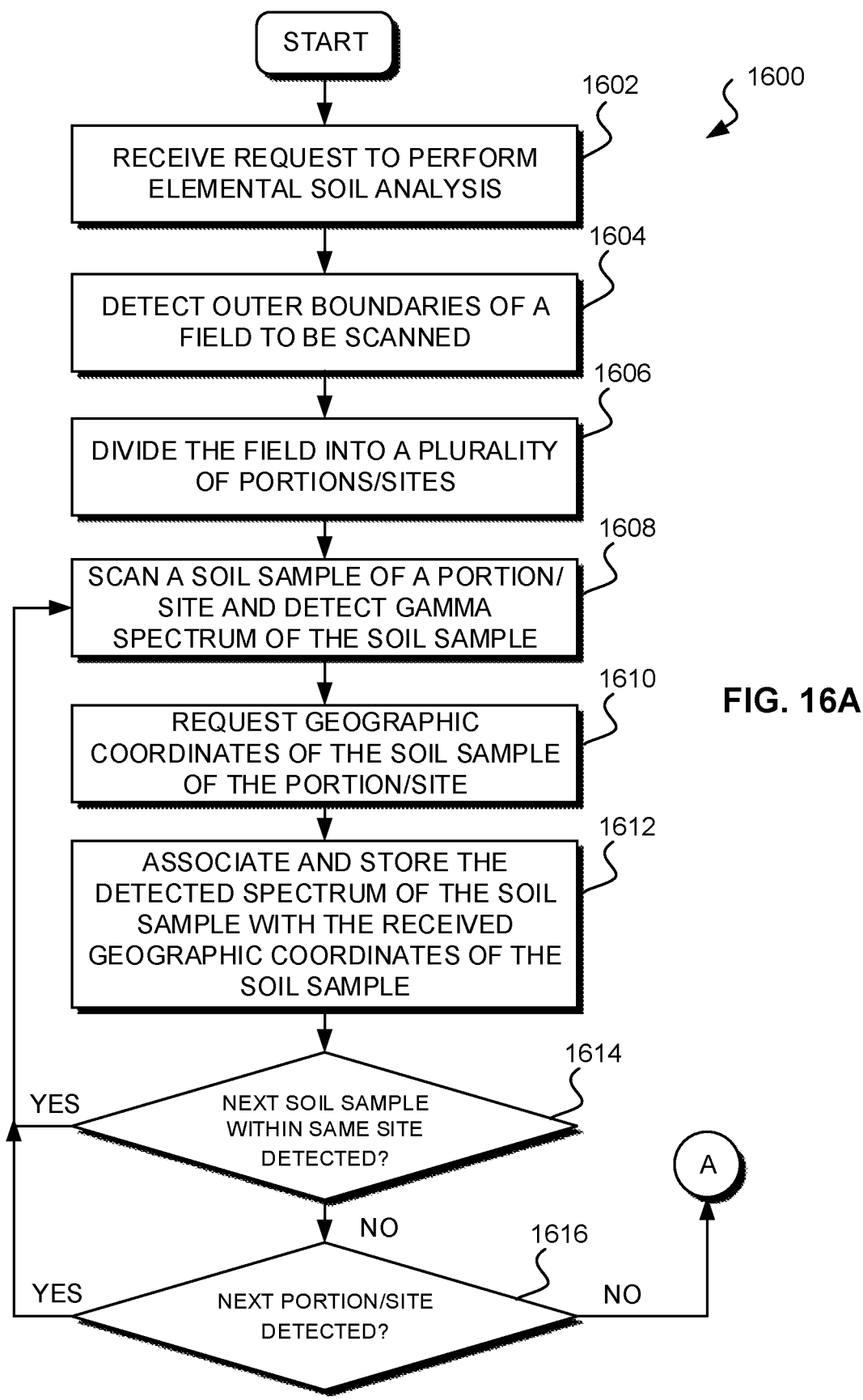
FIGS. 16A and 16B are block diagrams of an example process algorithm for determining elemental content of soil of a field.
Figure 16B:
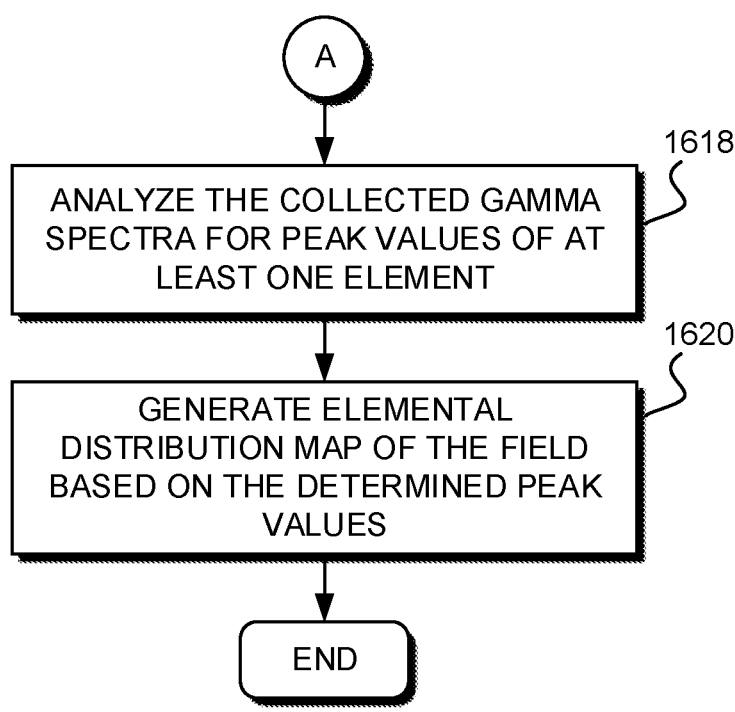

FIGS. 16A and 16B illustrate an example process 1600 for determining elemental content of soil 122 of the field 120. The process 1600 may begin at block 1602 where the processing unit 110 receives a request to perform an elemental soil analysis of a given field 120. In some examples, the request may be user- or system-generated. Furthermore, other methods for initiating elemental soil analysis process 1600 are also contemplated.

In response to the request, the processing unit 110, at block 1604, may detect one or more outer boundaries of the field 120 to be scanned. In one example, the processing unit 110 may detect the outer boundaries of the field 120 based on a digital rendering of a geographic map including at least a portion of the field 120 to be scanned, based on an actual scan of the field 120 (e.g., video, sonar, and so on), or some combination thereof. The geographic map analyzed during the outer boundary identification process may include approximate or exact geographic coordinates of the field 120, latitude and longitude of the field 120, area of the field 120, orientation of the field 120 with respect to four cardinal directions, and other data parameters sufficient to establish geospatial, relative, and specific location of the field 120.

At block 1606, the processing unit 110 may divide the field 120 to be scanned into a plurality of portions, or sites, 306. For example, the processing unit 110 may divide the field 120 into portions based on terrain profile, homogeneity or heterogeneity of the terrain, and/or presence or absence of terrain features, whether natural or man-made, such as hills, ridges, saddles, depressions, roads, structures, water features, vegetation, and so on. In some instances, each site 306 may comprise a relatively homogeneous terrain profile. During field division, the processing unit 110 of the system 100 may be configured to designate a separate site 306 in response to detecting a change in terrain, such as an asphalt road 308 crossing the field 120 and so on, and/or detecting a change in a profile and make-up of the terrain, e.g., in response to detecting a low spot in the terrain. Given the aforementioned terrain-related and other factors affecting scanning conditions, each site 306 of the plurality of sites 306 may vary in size from less than ~100 m² to ~1000 m² and greater, such that a given field 120 having a total area of approximately 800 m² may include twelve (12) sites and so on.

The processing unit 110 may be configured to, at block 1608, initiate scanning of a first soil sample of a first portion of the field 120. In one example, the processing unit 110 may use the neutron pulse source 102 to scan the first soil sample of the first portion/site 306. Additionally or alternatively, at block 1608, the processing unit 110 may be configured to detect, e.g., using the gamma detector 104, gamma spectrum of the first soil sample. At block 1610, the processing unit 110 may be configured to request geographic location of the first soil sample. In some instances, the processing unit 110 may be in communication with the GPS device 112, whether internal or external to the system 100, and may be configured to request and receive geographic coordinates or other geospatial positioning parameters indicative of a location of the first soil sample of the first portion 306 of the field 120.

The processing unit 110, at block 1612, may associate the detected gamma 116 spectrum data of the first soil sample and the received geographic coordinates of the first soil sample. In one example, the processing unit 110 may, at block 1612, store the scan data and the associated geographic coordinates in a data store device directly connected thereto. In other examples, the processing unit 110 may communicate with external, remote, or off-site storage servers, and/or cloud networking and data storage devices or systems.

At block 1614, the processing unit 110 may determine whether a next soil sample within a same one of the plurality of sites 306 has been detected. In one example, the processing unit 110 may detect a current geographic location of the system 100, e.g., of the structure 114, the neutron pulse source 102, and/or the gamma detector 104, the with respect to the area of the field 120 and/or area of the site 306 being scanned. Additionally or alternatively, the processing unit 110 may operate the system 100 to change its own geographic location, such that presence or absence of a next soil sample 124 and/or next site 306 may be determined. Other scenarios and methods for determining whether further data gathering needs to be performed by the system 100 are also contemplated. For instance, the system 100 may be configured to display a user notification requesting a confirmation that further soil samples 124 and/or sites 306 need to be scanned for elemental soil content analysis. In response to a next soil sample being available to be scanned within the current site 306, the processing unit 110 may return to block 1608 to scan the next available soil sample within the site 306.

In response to determining that all soil samples of the current site 306 have been scanned, the processing unit 110 may determine, at block 1616, whether a next one of the plurality of sites 306 has been detected. In one example, the processing unit 110 may detect a current geographic location of the system 100, e.g., of the structure 114, the neutron pulse source 102, and/or the gamma detector 104, with respect to the area of the field 120 and/or area of the site 306 being scanned. In response to determining, at block 1616, that a next site 306 of the plurality of sites 306 is available within the field 120 being scanned, the processing unit 110 may return to block 1608 to scan a first soil sample 124 within the next site 306 and so on. Additionally or alternatively, in response to all sites 306 of the field 120 having been scanned, the processing unit 110 may proceed to analyze the collected scan data.

At block 1618, the processing unit 110 may be configured to analyze the collected gamma spectra for one or more peak values of at least one of a plurality of elements, such as, but not limited to, C, Si, O, H, K, Cl, and so on. As described in reference to at least FIGS. 3-6 and 10-15, methodology for determining peak values of a given element may vary. In some instances, the processing unit 110 may be configured to identify midpoints, weighted centers, and other parameter values associated with elemental content analysis of the soil 120. Additionally or alternatively, the processing unit 110 may be configured to sort the identified peak values of each element by portion/site 306. Other operations and methods for analyzing collected spectra are also contemplated.

At block 1620, the processing unit 110 may be configured to generate an elemental distribution map based on gamma spectra data collected during the scanning operation using the system 100. As discussed previously, the elemental distribution map may be generated using a local polynomial interpolation or another computational approach and may be superimposed on a geographical base map. The generated elemental distribution map may include an arrow or another type of icon indicative of one or more cardinal directions, such as north, south, east, and west, to indicate directional orientation of the map. In other examples, the generated elemental distribution map may be automatically oriented such that an upward vertical direction signifies northward direction and so on. In some instances, the generated map may include a corresponding legend and/or a scale bar indicating one or more ranges of elemental content of a given element or a plurality of elements. The generated elemental distribution map may comprise a contour map including one or more contour value labels indicating regions with the same content.

The process 1600 may then end. In some instances, the processing unit 110 may be configured to repeat one or more processes for generating elemental distribution map based on the collected gamma spectra data.

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There exists a plurality of advantages of the present disclosure arising from the various features of the apparatus, systems, and methods described herein. It will be noted that alternative embodiments of the apparatus, systems, and methods of the present disclosure may not include all of the features described, yet still benefit from at least some of the advantages of such features. Those of ordinary skill in the art may readily devise their own implementations of the apparatus, systems, and methods that incorporate one or more of the features of the present disclosure.

The invention claimed is:

1. A system for analyzing an elemental content of a surface layer of a geographic area, the system comprising:
 a plurality of gamma detectors, each gamma detector being configured to detect at least one gamma ray spectrum at each of a plurality of locations of the geographic area; and
 a processor communicatively coupled to each of the plurality of gamma detectors, the processor configured to:
  in response to receiving the detected at least one gamma ray spectrum, associate the detected at least one gamma ray spectrum with geographic coordinates of a location of the plurality of locations of the geographic area of the detected at least one gamma ray spectrum,
  determine an amount of at least one element at each location of the plurality of locations based on a life time of the detected at least one gamma ray spectrum at the respective location, wherein the life time of the detected at least one gamma ray spectrum is an average of life times of each gamma detector of the plurality of gamma detectors, and generate a concentration of the at least one element within the surface layer of the geographic area based on the amount of the at least one element at each of the plurality of locations.

2. The system of claim 1, wherein a surface area of the geographic area is divided into a plurality of portions, and wherein the plurality of locations includes at least one location within each of the plurality of portions.

3. The system of claim 1, further comprising:
a neutron generator,
wherein each detected at least one gamma ray spectrum results from neutron pulsing generated by the neutron generator.

4. The system of claim 1, wherein the at least one element includes at least one of carbon (C), silicon (Si), potassium (K), oxygen (O), hydrogen (H), and chlorine (Cl).

5. A method for analyzing an elemental content of a surface area of a geographic area, the method comprising:
dividing, by a processor, the surface area into a plurality of locations;
scanning, by a gamma detector communicatively coupled to the processor, at least a portion of each location of the plurality of locations of the surface area of the geographic area to detect a gamma ray spectrum of a surface layer of the at least a portion;
associating, by the processor communicatively coupled to the gamma detector, the detected gamma ray spectrum with geographic coordinates of a portion of that detected gamma ray spectrum;
calculating, by the processor, based on the detected gamma ray spectrum at the portion, an amount of at least one element at the portion of the respective location of the plurality of locations of the surface area of the geographic area; and
generating, by the processor, a map indicating a concentration of the at least one element within the surface area of the geographic area.

6. The method of claim 5, wherein the at least one element includes at least one of carbon (C), silicon (Si), potassium (K), oxygen (O), hydrogen (H), and chlorine (Cl).

7. The method of claim 5, wherein each location of the plurality of locations has a homogeneous landscape.

8. The method of claim 5, wherein the detected gamma ray spectrum results from neutron pulsing generated by a neutron generator.

9. The method of claim 5, further comprising correcting an energy of the detected gamma ray spectrum based on a predefined value.

10. A system for analyzing an elemental content of a surface layer of a geographic area, the system comprising:
a plurality of gamma detectors, each gamma detector configured to detect gamma spectra of a predefined portion of the surface layer of the geographic area,
wherein each gamma detector scans the surface layer of the geometric area while being movably transferred over the surface layer of the geometric area, and
wherein at least one gamma detector of the plurality of gamma detectors corrects an energy of the gamma spectra;
a geographic positioning device configured to receive geographic coordinates of the predefined portion of the surface layer of the geometric area; and a processor communicatively coupled to the plurality of gamma detectors and the geographic positioning device, the processor configured to:
associate the corrected gamma spectra having the corrected energy of the predefined portion of the surface layer of the geometric area with the geographic coordinates of the predefined portion of the surface layer of the geometric area,
calculate, based on a life time of a gamma spectrum, a weight percent of an element within the predefined portion of the surface layer of the geometric area,
wherein the life time of the gamma spectrum is an average of life times of each gamma detector of the plurality of gamma detectors, and
generate a map indicating a concentration of the element within the predefined portion of the surface layer of the geographic area based on the calculated weight percent of the element within the predefined portion of the surface layer of the geographic area,
wherein each gamma detector corrects the energy of the gamma spectra based on a predefined value determined via a spectra-shifting and weight-percent calculation executed by each gamma detector or the processor.

11. The system of claim 10, further comprising:
a pulsed fast thermal neutron system.

12. The system of claim 11, wherein the pulsed fast thermal neutron system includes a neutron generator.

13. The system of claim 10, wherein each gamma detector is configured to detect the gamma spectra of at least one soil sample from the surface layer of the geographic area based on gamma rays naturally emanating from the at least one soil sample.

14. The system of claim 13, wherein the at least one soil sample comprises a plurality of soil samples, and wherein the plurality of soil samples cumulatively comprises at least 10% of a surface area of a field of the surface layer of the geographic area.

15. The system of claim 13, wherein the concentration of the element within the at least one soil sample is indicative of a content of at least one of carbon (C), silicon (Si), potassium (K), oxygen (O), and hydrogen (H).

16. The system of claim 15, wherein the processor is further configured to determine a content of carbon (C) within the at least one soil sample based on an average of net gamma spectra detected within a portion of a field, and wherein the processor is further configured to determine a content of potassium (K) based on gamma rays naturally emanating from the at least one soil sample.

17. The system of claim 10, wherein the spectra-shifting and weight-percent calculation is configured to shift the gamma spectra such that, for each gamma spectra of a plurality of gamma spectra, centroids of dominant peaks of the element are associated with a same one of a plurality of energy channels of the gamma spectra.

18. The system of claim 10, wherein the average of life times of each gamma detector of the plurality of gamma detectors is based on a real measurement time, an input count rate, and an output count rate.

19. The system of claim 10, wherein the processor is further configured to associate the calculated weight percent of the element with a geographical middle point between two neighboring records.

* * * * *